US012569332B2

(12) United States Patent     (10) Patent No.:    US 12,569,332 B2

Wu                          (45) Date of Patent:    *Mar. 10, 2026

(54) IOL INJECTOR WITH AUTOMATIC DRIVER OR ASSISTED MANUAL DRIVE FORCE

(71) Applicant: Alcon Inc., Fribourg (CH)

(72) Inventor: Yinghui Wu, Cedar Hill, TX (US)

(73) Assignee: Alcon Inc., Fribourg (CH)

( * ) Notice: Subject to any disclaimer, the term of this patent is extended or adjusted under 35 U.S.C. 154(b) by 731 days.

This patent is subject to a terminal disclaimer.

(21) Appl. No.: 17/817,728

(22) Filed: Aug. 5, 2022

(65) Prior Publication Data

US 2022/0370194 A1     Nov. 24, 2022

Related U.S. Application Data

(62) Division of application No. 16/712,216, filed on Dec. 12, 2019, now Pat. No. 11,439,500.

(60) Provisional application No. 62/782,387, filed on Dec. 20, 2018.

(51) Int. Cl.
*A61F 2/16*         (2006.01)

(52) U.S. Cl.
CPC ..................................... *A61F 2/167* (2013.01)

(58) Field of Classification Search
CPC .................. A61F 2/167; A61F 2/1672; A61M 2210/0612
See application file for complete search history.

(56) References Cited

U.S. PATENT DOCUMENTS

| | | | | |
|---|---|---|---|---|
| 4,681,102 A | * | 7/1987 | Bartell | .................. A61F 2/1678 606/1 |
| 2014/0276901 A1 | * | 9/2014 | Auld | ..................... A61F 2/1678 606/107 |
| 2017/0043097 A1 | * | 2/2017 | Jones | ....................... A61M 5/24 |
| 2018/0256393 A1 | * | 9/2018 | Yamamoto | .............. A61P 29/00 |

* cited by examiner

*Primary Examiner* — Ashley L Fishback
*Assistant Examiner* — Chima U Igboko
(74) *Attorney, Agent, or Firm* — Patterson + Sheridan, LLP

(57) ABSTRACT

An IOL injector having an automatic plunger advancement driver is described. In addition, an IOL injector having a spring-assisted driving mechanism and a spring damping mechanism is described.

4 Claims, 14 Drawing Sheets

IOL INJECTOR WITH AUTOMATIC DRIVER OR ASSISTED MANUAL DRIVE FORCE

PRIORITY CLAIM

This application is a divisional of U.S. Non-Provisional patent application Ser. No. 16/712,116, filed on Dec. 12, 2019, and claims the benefit of priority of U.S. Provisional Patent Application Ser. No. 62/782,387 titled "IOL INJECTOR WITH AUTOMATIC DRIVER OR ASSISTED MANUAL DRIVE FORCE," filed on Dec. 20, 2018, whose inventor is Yinghui Wu, which is hereby incorporated by reference in its entirety as though fully and completely set forth herein.

TECHNICAL FIELD

The present disclosure relates to intraocular lens (IOL) injectors.

BACKGROUND

The human eye in its simplest terms functions to provide vision by transmitting and refracting light through a clear outer portion called the cornea, and further focusing the image by way of the IOL onto the retina at the back of the eye. The quality of the focused image depends on many factors including the size, shape, and length of the eye, and the shape and transparency of the cornea and IOL. When trauma, age, or disease cause the IOL to become less transparent, vision deteriorates because of the diminished light which can be transmitted to the retina. This deficiency in the IOL of the eye is medically known as a cataract. The treatment for this condition is surgical removal of the IOL and implantation of an artificial IOL ("IOL").

Many cataractous lenses are removed by a surgical technique called phacoemulsification. During this procedure, an opening is made in the anterior capsule of an eye and a phacoemulsification cutting tip is inserted into the diseased IOL and vibrated ultrasonically. The vibrating cutting tip liquifies or emulsifies the IOL so that the IOL may be aspirated out of the eye. The diseased IOL, once removed, is replaced with an IOL.

The IOL may be injected into the eye through a small incision, sometimes same incision used to remove the diseased IOL. An IOL injector may be used to deliver an IOL into the eye.

SUMMARY

According to first aspect, the present disclosure relates to an IOL injector. The IOL injector has an injector body having a proximal end and a distal end. The injector body includes: a main injector body having a distal end and a proximal end; a nozzle coupled to the distal end of the main injector body; and a bore extending from the proximal end of the injector body to the distal end of the injector body. The IOL injector also has a plunger having a proximal portion and a distal portion, the plunger slideably disposed within the bore and adapted to advance an IOL along a longitudinal axis of the IOL injector. The IOL injector also has an automatic plunger advancement driver having: a cylinder concentrically disposed around the proximal portion of the plunger, the cylinder having a thread adapted to rotatably engage with a plunger thread in the proximal portion of the plunger; a torsion spring having stored rotational energy, the torsion spring concentrically disposed around the cylinder, wherein at least one end of the torsion spring is coupled to the cylinder such that in response to a release of the stored rotational energy, the cylinder is configured to rotate around the longitudinal axis and the plunger moves axially toward the distal end of the injector body.

According to a second aspect, the present disclosure relates to an IOL injector. The IOL injector has an injector body having a proximal end and a distal end. The injector body includes a main injector body having a distal end and a proximal end; a nozzle coupled to the distal end of the main injector body; and a bore extending from the proximal end of the injector body to the distal end of the injector body. The IOL injector also has a plunger having a proximal end and a distal end, the plunger slideably disposed within the bore and adapted to advance an IOL along a longitudinal axis of the IOL injector. The IOL injector also has a spring-assisted driving mechanism including one or more assistive springs having stored elastic energy, wherein the assistive springs are directly or indirectly coupled at a first end of the spring to the plunger and at a second end of the spring to the injector body, such that movement of the plunger toward the distal end of the injector body is assisted by release of elastic energy from the spring. The IOL injector also has a spring damping mechanism including one or more resistive springs directly or indirectly coupled at a first end of the spring to the plunger and at a second end of the spring to the injector body, such that elastic energy is stored in the resistive springs in response to axial movement of the plunger toward the distal end of the injector body.

The various aspects may include one or more of the following features. The IOL injector may have a braking mechanism configured to prevent axial movement of the plunger, including: a handle having a proximal end and a distal end and rotatably coupled to the injector body at a pivot point disposed between the proximal end and the distal end of the handle in response to a force applied to the handle; a brake release arm having a proximal end coupled to the handle and the distal end coupled to one or more brake pads adapted to apply a frictional braking force to the plunger in absence of a force applied to the handle; compression springs disposed between the injector body and the brake pads, the compression springs adapted to move the brake pads toward the plunger; wherein, in response to the force applied to the handle, the brake release arm compresses the compression springs and moves the brake pads away from the plunger thereby removing the frictional braking force from the plunger and allowing movement of the plunger in response to the release of the stored rotational energy of the torsion spring. The IOL injector may have a hydraulic damping mechanism including: a proximal chamber having approximal end and a distal end; a distal chamber having a proximal end and a distal end; an orifice fluidically coupling the proximal chamber to the distal chamber; the proximal portion of the plunger having a proximal piston slideably disposed within the proximal chamber; and the distal portion of the plunger having a distal piston slideably disposed within the distal chamber; wherein: the proximal piston is movable from the proximal end of the proximal chamber to the distal end of the proximal chamber in response to movement of the threaded cylinder-engaging portion of the plunger; the orifice allows movement of a hydraulic fluid from the proximal chamber to the distal chamber in response to movement of the proximal piston; and the distal piston is movable from the proximal end of the distal chamber to the distal end of the distal chamber in response to movement of the fluid. The IOL injector may have a braking mechanism configured to prevent axial movement of the plunger, including: a handle having a proximal end and a distal end and rotatably coupled to the injector body at a pivot point disposed between the proximal end and the distal end of the handle in response to a force applied to the handle; a hydraulic flow barrier having a first end coupled to the handle and a second end slideably disposed within the orifice and adapted to prevent movement of the fluid through the orifice from the proximal chamber to the distal chamber in absence of a force applied to the handle; and a hydraulic flow gate forming a passage adapted to allow movement of the fluid through the orifice when the hydraulic flow gate is disposed in the orifice; compression springs disposed between the handle and the orifice, the compression springs adapted to move the hydraulic flow gate out of the orifice; wherein: in response to application of a force to the handle, the hydraulic flow gate is moved into the orifice and allows movement of the fluid through the orifice from the proximal chamber to the distal chamber. The IOL injector may include an IOL disposed within a hollow portion of the nozzle, such that the axial movement of the plunger towards the distal end of the injector body causes the IOL to be ejected from the nozzle. The IOL injector may have a spring-assisted driving mechanism including one or more assistive spring-driven gears, having: a first spring having stored elastic energy coupled at a first end to a first gear rotatably coupled to the injector body and the first spring coupled at a second end to the injector body; a rack disposed on the plunger, the rack having teeth adapted to rotatably mesh with teeth of the first gear; wherein the first gear is adapted to rotate in response to release of the stored elastic energy from the first spring; and the plunger is adapted to move axially toward the distal end of the injector body in response to rotation of the first gear; the spring-assisted driving mechanism thereby assisting the axial movement of the plunger; and a spring damping mechanism having one or more damping spring-driven gears, having: a second spring coupled at a first end to a second gear rotatably coupled to the injector body and the second spring coupled at a second end to the injector body; wherein the second gear is adapted to rotate in response to axial movement of the plunger toward the distal end of the injector body; and the second spring is adapted to store elastic energy in response to the rotation of the second gear; the spring damping mechanism thereby providing resistance to the axial movement of the plunger. In some implementations of the IOL injector, in response to an application of an axial force by a user to the plunger to advance the plunger toward the distal end of the injector body, the rack engages the first gear and the first gear applies a force to assist further advancement of the plunger through the bore; and in response to further application of axial force by a user to the plunger to advance the plunger toward the distal end of the injector body, the rack engages the second gear and the second gear applies a force to resist further advancement of the plunger through the bore. The first spring and/or the second spring may be a tension spring. The first spring and/or the second spring may be a compression spring. The IOL injector may have an assistive tension spring coupled at a proximal end of the tension spring to the plunger and at a distal end of the tension spring to a sheath, wherein the tension spring is disposed within the sheath and a portion of the plunger is disposed within the tension spring; a damping compression spring coupled at a proximal end to the sheath and at a proximal end to at least one stop coupled to an inner wall of the injector body, wherein the disposed within the compression spring; wherein: the plunger moves axially toward the distal end of the injector body in response to release of elastic energy from the tension spring; and the compression spring is adapted to store elastic energy in response to movement of the plunger toward the distal end of the injector body. The IOL injector may have an assistive compression spring coupled at a proximal end of the assistive compression spring to the proximal end of the injector body and at a distal end of the assistive compression spring to the plunger; a resistive compression spring coupled at a distal end of the resistive compression spring to the distal end of the injector body; a first removable stop disposed within the bore at a proximal portion of the injector body; a second removable stop disposed within the bore at a distal portion of the injector body; wherein: in a first configuration, the first stop is adapted to contact the assistive compression spring, thereby maintaining the assistive compression spring in a compressed state having stored elastic energy; in a second configuration, the first stop is removed from the bore, and in response, the assistive compression spring is configured to expand and in response the plunger is configured to move axially toward the distal end of the injector body until the assistive compression spring contacts the second stop; in a third configuration, the second stop is also removed from the bore, and in response, the assistive compression spring is configured to expand and contact the resistive compression spring, and in response: the plunger is configured to move further axially toward the distal end of the injector body, and the resistive compression spring is configured to compress, wherein a compression of the resistive compression spring provides a resistive force in opposition to the movement of the plunger. In the second configuration, a plunger tip of the plunger may be configured to move to a location proximally adjacent to an IOL dwell position. In the third configuration, a plunger tip of the plunger may be configured to move to the distal end of the injector body.

BRIEF DESCRIPTION OF THE DRAWINGS

For a more complete understanding of the present disclosure, reference is now made to the following description, taken in conjunction with the accompanying drawings, which are not to scale, and in which.

DETAILED DESCRIPTION

Figure 1:
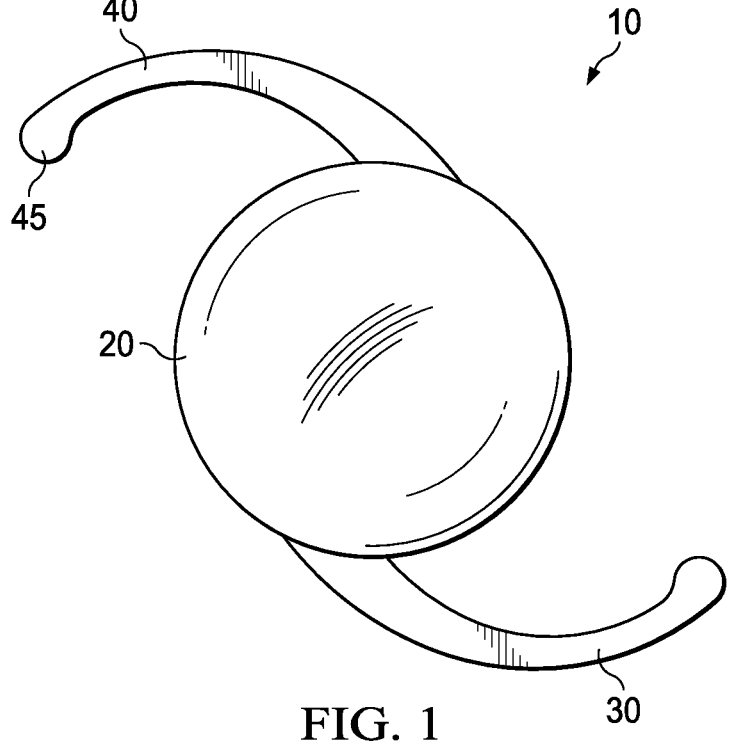
FIG. 1 shows an example IOL.

For the purposes of promoting an understanding of the principles of the present disclosure, reference will now be made to the implementations illustrated in the drawings, and specific language will be used to describe the same. It will nevertheless be understood that no limitation of the scope of the disclosure is intended. Any alterations and further modifications to the described IOL injectors, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

Due to the sensitivity and delicacy of ocular tissues and structures, it is helpful for the user to be able to advance an IOL during implantation with acceptable peak speed and force. However, inherent to the mechanism of compressing and advancing the IOL into the eye, there is a large pressure release when the IOL is at the exit of the nozzle of the IOL injector. In some cases, this causes the IOL to be ejected with high velocity and in a less controllable manner. Pressure and force variations during injection reduce user control of the injector, which increases the risk of IOL sudden ejection. Therefore, injectors of the present disclose may help ensure that the mechanism and magnitude of force applied through user interaction is appropriate and repeatable. The injectors may also be intuitive to operate and able to be used by medical personnel over a wide spectrum of skills and techniques.

The present disclosure relates to systems, apparatuses, and methods for delivering an IOL into an eye.

FIG. 1 shows an example IOL 10. The IOL 10 is a one-piece IOL that includes a optic 20, a leading haptic 30, and a trailing haptic 40. Each of the haptics 30 and 40 has a freely extending end 45.

In some implementations, the IOL 10 may be a one-piece IOL. That is, in some implementations, the IOL 10 may include an optic 20 and haptics 30 and 40, as shown in FIG. 1. In some implementations, the optic 20 and the haptics 30 and 40 may be integrally formed out of a single piece of material. In other implementations, the optic 20 may be formed out of one piece of material; the haptics 30 and 40 may be formed out of another piece of material; and the optic 20 and the haptics 30 and 40 may be coupled together prior to delivery into an eye. In some instances, the optic 20 and haptics 30 and 40 may be fixedly secured to each other prior to insertion into an IOL injector and delivered into an eye.

Figure 12:
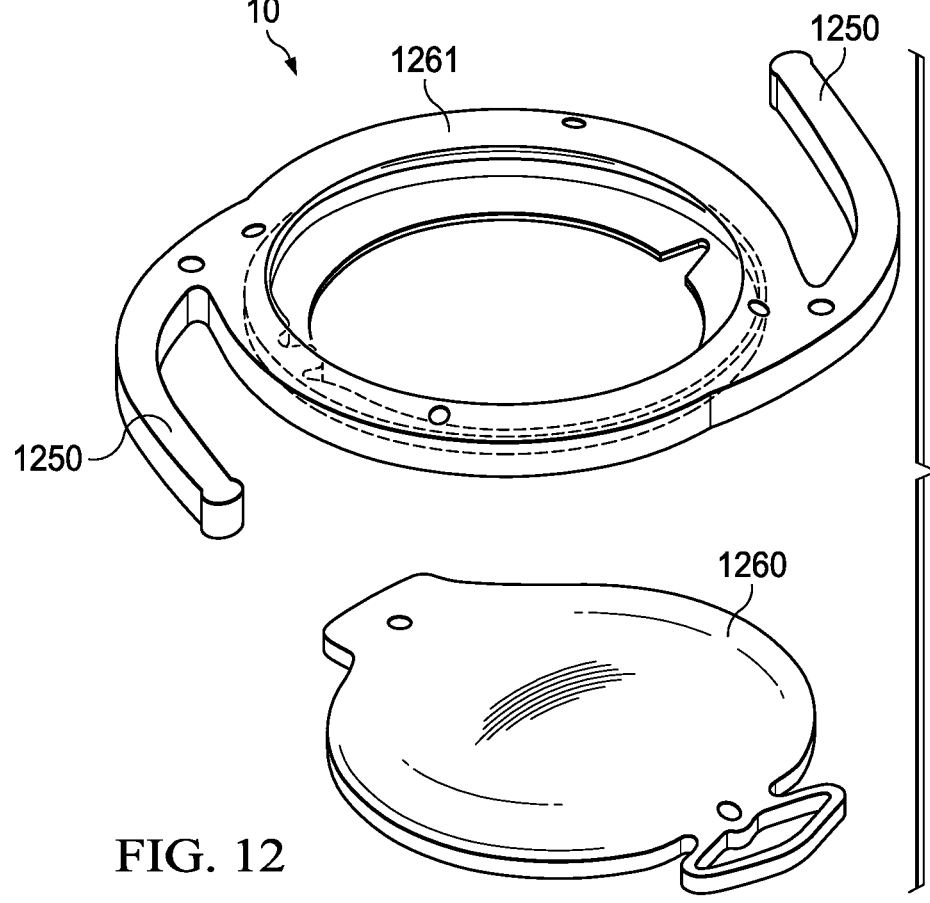
FIG. 12 shows an exemplary 2-piece IOL including a base and an optic.

In other implementations, the IOL 10 may be a multi-piece IOL, as shown, for example in FIG. 12. For example, in some implementations, the IOL 10 may include two or more separate components. FIG. 12 is an example IOL 10 that includes two removably attached components. As shown in FIG. 12, the IOL 10 includes an optic 1260 and a base 1261 that includes haptics 1250. The base 1261 may be a hollow base. The optic 1260 and the base 1261 are adapted to be coupled together into a unitary IOL and, thereafter, detached from each other into separate components, if desired. In some instances, one or more components of a multi-piece IOL, such as, for example the two-piece IOL 10 shown in FIG. 12, are separately injectable into a patient's eye. Once in the eye, the components may be assembled into a complete IOL. For example, the two-piece IOL 10 shown in FIG. 12, the optic 1260 and the base 1261 are separately injectable into an eye. Once injected, the optic 1260 is adapted to be coupled to and to rest on the base 1261.

Figure 2:
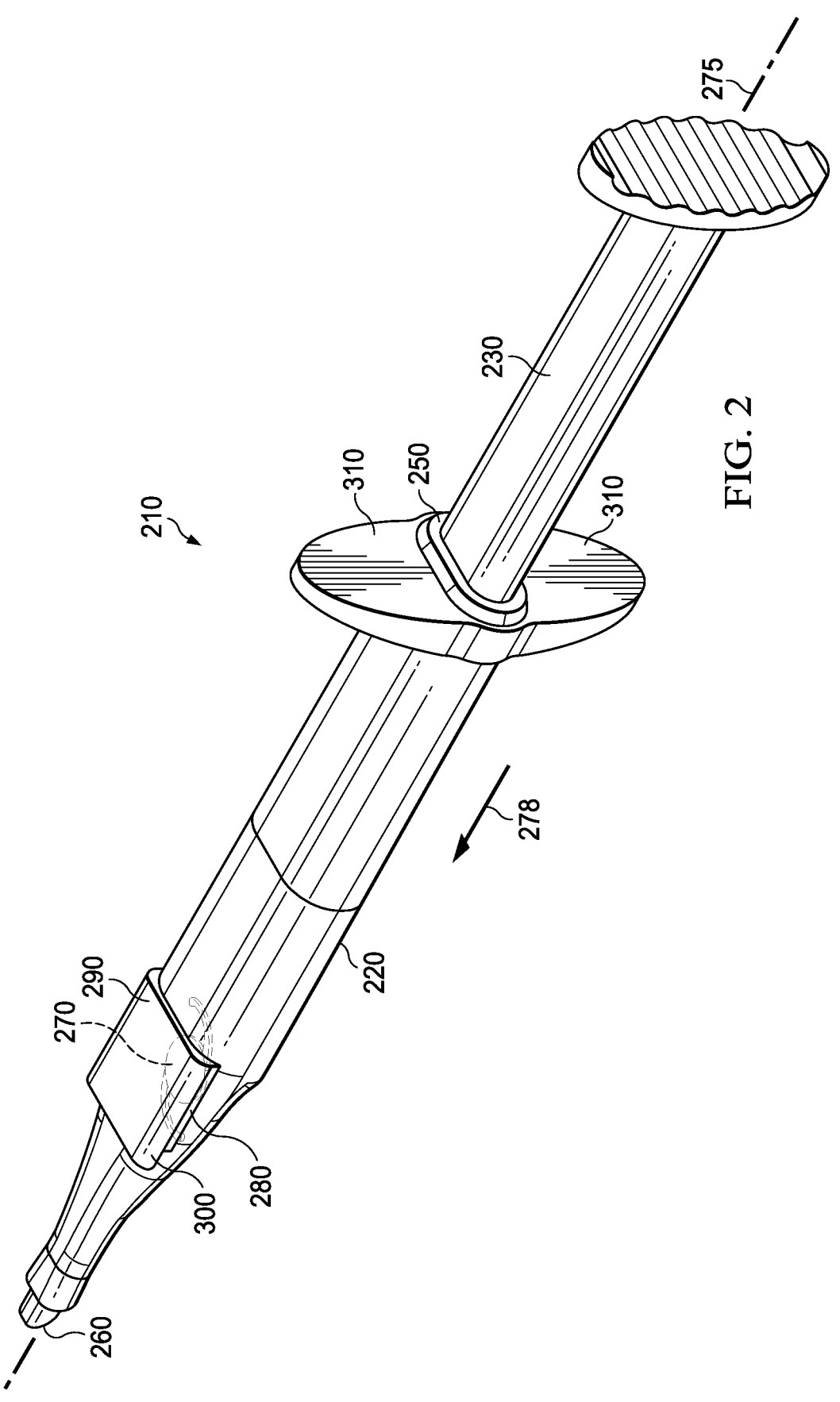
FIG. 2 is a perspective view of an example IOL injector actuated by manual user application of force.
Figure 3:
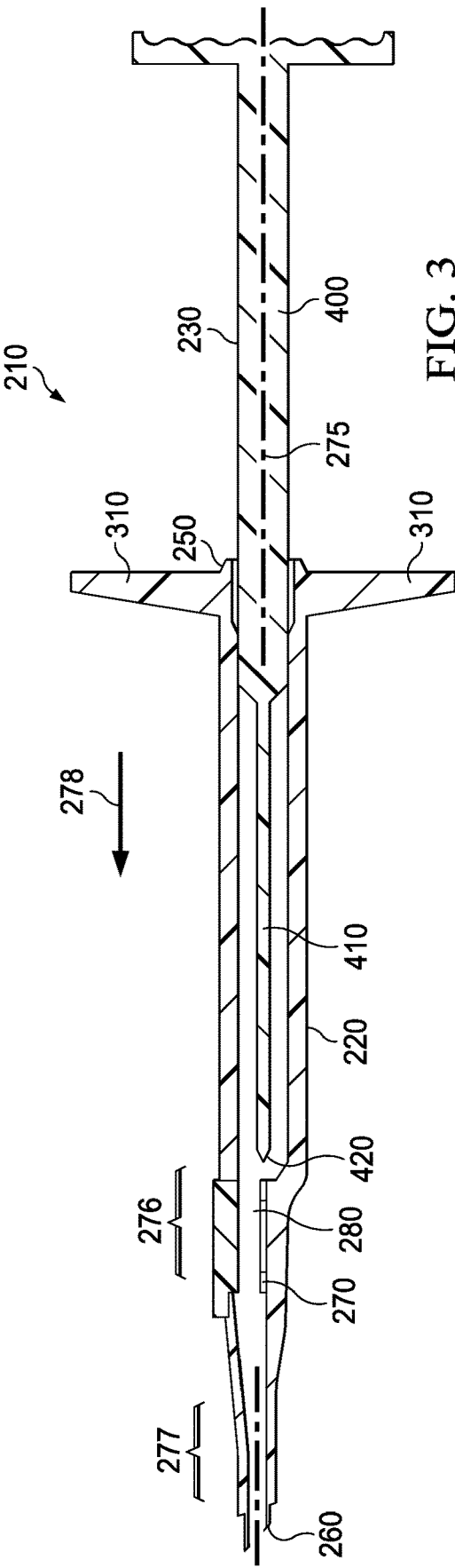
FIG. 3 is a longitudinal cross-sectional view of the IOL injector actuated by manual user application of force.

FIGS. 2 and 3 are exemplary schematics of an IOL injector 210 that is actuated by manual user application of force. The IOL injector 210 includes an injector body 220, a plunger 230 adapted to reciprocate through a bore formed in the injector body 220, a folding device 276 and a nozzle 277 disposed at a distal end 260 of the injector body 220.

The IOL injector 210 also includes a longitudinal axis 275. The longitudinal axis 275 may extend along the plunger 230 and define a longitudinal axis of the plunger 230.

The nozzle 277 defines a passage through which a folded IOL may be advanced and delivered into an eye via an opening at distal end 260. A delivery channel 280 of the folding device 276 may be aligned with the bore and the passage through which the folded IOL may be advanced and delivered into an eye. The folding device 276 is shown schematically may be any folding device capable of folding an unfolded IOL 270 for delivery into an eye. The bore, the delivery channel 280 of the folding device 276, and the passage through which the folded IOL may be advanced and delivered into an eye may combine and extend from proximal end 250 to distal end 260 of the injector body 220. The plunger 230 is received within the bore and may be moveable therein such that the plunger 230 is slideable within the bore. Particularly, the plunger 230 may be slideable within the bore in order to advance an IOL, such as IOL 270, within the delivery channel 280 of the folding device 276 and the passage of the nozzle 277 to allow delivery into the eye.

The folding device 276 may include a door 290 to provide access to the interior of the folding device 276. The door 290 may include a hinge 300 such that the door 290 may be pivoted about the hinge 300 to open the folding device 276 and, for example, allow the installation of the IOL 270. In other implementations, the folding device 276 may exclude a door for installing the IOL 270. In such instances, the IOL 270 may be incorporated into the folding device 276 at the time of assembly of the folding device 276. This, in such instances, the IOL injector 210 would be a preloaded IOL injector.

The injector body 220 may also include tabs 310 formed at the proximal end 250 of the injector body 220. The tabs 310 may be manipulated by fingers of a user, such as an ophthalmologist, an ophthalmic surgical assistant or nurse, or other medical profession, to advance the plunger 230 through the bore. The plunger 230 may include a body portion 400, a plunger rod 410 extending distally from the body portion 400, and a plunger tip 420 formed at the distal end of the plunger rod 410 and adapted to contact the folded IOL disposed, for example, within the folding device 276 of the IOL injector 210. As the plunger 230 is displaced distally within the bore in the direction of the arrow 278, the plunger 230 engages and advances the folded IOL, such as IOL 270, contained in the folding device 276.

In some implementations described herein, various parts of the plunger 230 may be physically separated or decoupled from each other within the injector body 220 of the IOL injector 210. For example, in some implementations, the body portion 400 may be physically separated or decoupled from the plunger rod 410. In various implementations, where various parts of the plunger 230 are physically separated or decoupled from each other, additional components of the IOL injector 210 may actuate movement of one part of the plunger 230 in response to movement of another part of the plunger 230, as will be apparent to persons of ordinary skill in the art upon reading of the present disclosure.

Occasionally, patients may require replacement of an IOL, and a procedure to replace an IOL may result in damage to the eye. With the use of a two-piece IOL, for example, a replacement procedure may involve replacement only of the optic, allowing the base to remain in place within the eye.

Figure 10:
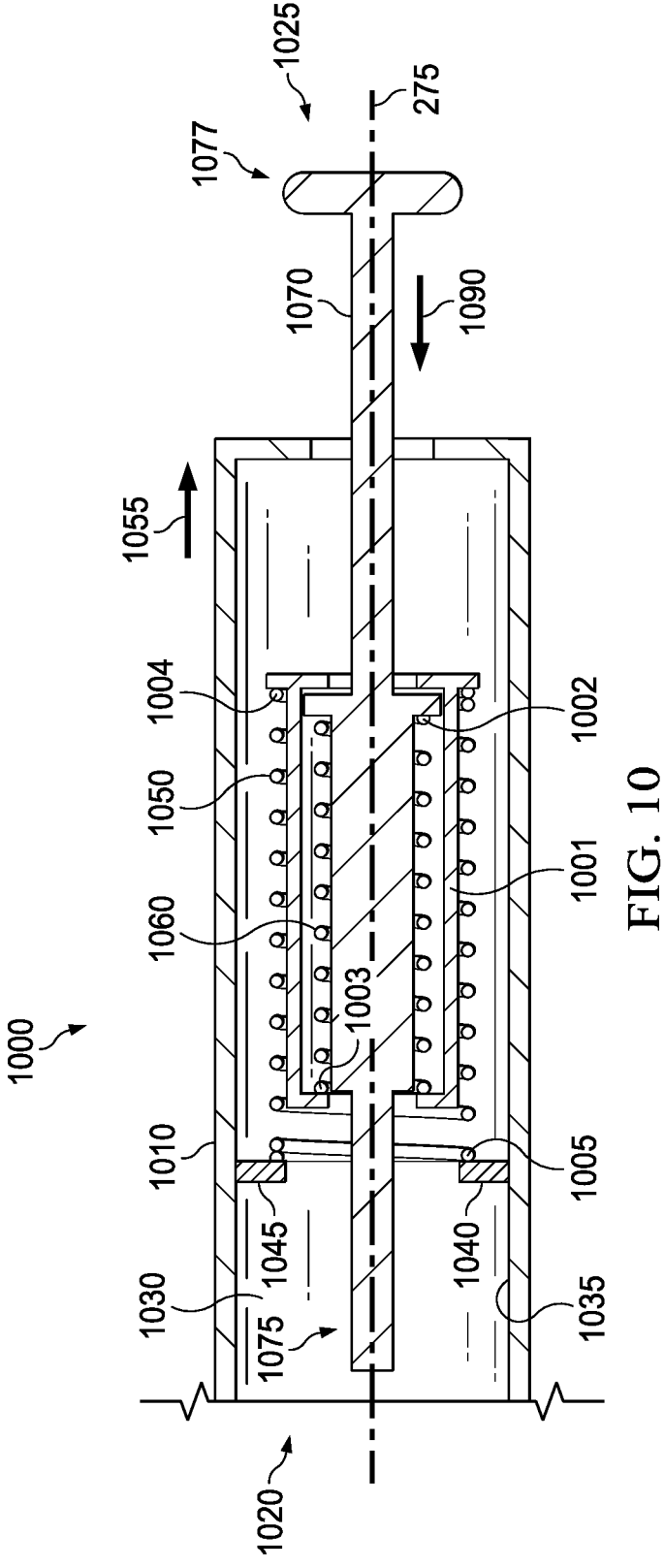
FIG. 10 is a cross-sectional view of another example IOL injector with helical spring assisted manual drive force.

As explained above, in some implementations, the IOL 10 may be a two-piece IOL, as shown, for example, in FIG. 10. The IOL 10 includes the base 1261 and the optic 1260 are separately injected into the patient's eye. Accordingly, for two-piece IOLs, the base 1261 and the optic 1260 may be contained in separate IOL injectors for insertion in the eye. In other implementations, the two components of a two-piece IOL may be inserted into an eye separately using a single IOL injector. For a single piece IOL (as shown, for example in FIG. 1), the optic 20 and haptics 30 and 40 form a unitary IOL and is insertable into an eye as a single unit with the use of a single IOL injector.

Accordingly, in some implementations, a user may place a one-piece IOL into an IOL injector, for example, by loading an IOL into the IOL storage compartment of the IOL folding device of the IOL injector. In some implementations, the IOL may be manually folded into a compressed or folded configuration prior to installation into the IOL injector. The IOL may then be further compressed or folded by the folding device, or the IOL injector may lack a folding device and may simply include an IOL storage compartment in the place of the folding device.

In the case of a two-piece IOL, in some implementations, a user may load the base (which may be similar to base 1261) into an IOL storage compartment of an IOL injector, for example, via a door. The optic (which may be similar to optic 1260) may be introduced into the IOL storage compartment of separate IOL injector, for example, via a door. In some instances, the IOL storage compartment may be accessed through the door similar to door 290. In some implementations, one or both of the base and the optic may be manually folded into a compressed or folded configuration prior to installation into an IOL injector.

In some implementations, the IOL may be pre-loaded into the storage compartment of an IOL injector, for example, during manufacturing or otherwise prior to distribution to an end user. Accordingly, for the one-piece IOL, the one-piece IOL may be pre-loaded into the storage compartment an IOL injector prior to receipt by the end user. For a two-piece IOL, the base may be pre-loaded into a storage compartment of one IOL injector, while the optic may be pre-loaded into the IOL storage compartment of another IOL injector. The term "pre-loaded" as used herein means that an IOL, either in a one-piece or multi-piece configuration (including, for example, a two-piece configuration) is loaded into the IOL injector not by a user, but, rather, the IOL is installed in the IOL injector before and is already contained within the IOL injector when the IOL injector is received by the user. The IOL injector(s) may be packaged within sterile packaging when received by a user.

As would be understood by persons of ordinary skill in the art, an IOL that is pre-loaded into an IOL injector has advantages over manual installation and folding of an IOL into the IOL injector that is performed by a user. For example, manual installation and folding of an IOL may allow more opportunity for errors, which have the potential to cause unnecessary secondary manipulation or correction during an already complex procedure. Manual installation and folding of an IOL may also introduce the possibility of contamination of the IOL, such as by human error or poor sterile technique. Contamination of the IOL may compromise the sterile environment for the patient and risk infection or other harm to the patient.

Figure 4:
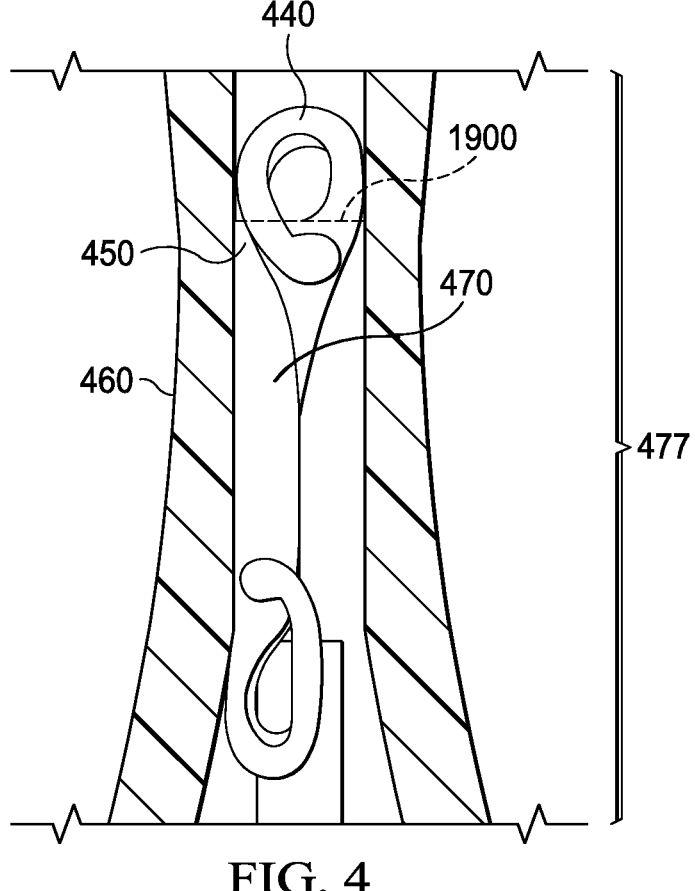
FIG. 4 is a view of a distal end of an IOL injector with an IOL located therein at a dwell position.

FIG. 4 shows a view of the distal end 460 of the IOL injector 210 with an IOL 470 located therein at a dwell position 477. The dwell position 477 in FIG. 4 may correspond to a location in the nozzle 277 shown in FIG. 3. As shown in FIG. 4, the dwell position 477 of the IOL 470 may be defined as a location where a distal edge of an optic 450 of the IOL 470 substantially aligns with the demarcation 1900. A haptic 440 or a portion thereof may extend beyond the demarcation 1900.

In various implementations described herein and within the scope of the description as would be understood by persons of ordinary skill in the art, the IOL injectors of the present disclosure include one or more springs. In some implementations, the springs are configured to provide a mechanical force to drive or assist axial advancement of the plunger toward the distal end of the IOL injector. In some implementations, the springs are configured to provide a mechanical force in opposition to axial advancement of the plunger toward the distal end of the IOL injector, thereby providing a damping or resistive force to axial advancement of the plunger toward the distal end of the IOL injector body.

The term "spring" as used herein refers to an elastic object that stores mechanical energy. More specifically, a spring is a IOL injector that stores potential energy, specifically elastic potential energy, by straining the bonds between the atoms of an elastic material.

There are various types of springs, such as coil springs and torsion springs, that can be used in various implementations of the IOL injectors described herein and within the scope of the present disclosure.

For example, when a helical spring, otherwise known as a coil spring, is compressed or stretched from its resting position, it exerts an opposing force approximately proportional to its change in length. The term "resting position" as used herein refers to a spring having essentially no stored elastic energy. Coil springs are typically of two types: tension springs or compression springs. Tension or extension springs are designed to become longer under load. Their turns (loops) are typically touching in the unloaded position, and they may have a hook, eye or other means of attachment at each end. In contrast, compression springs are designed to become shorter when loaded. Their turns (loops) are typically not touching in the unloaded position, and they typically need no attachment points such as those used for tension springs.

A torsion spring is a spring that works by torsion or twisting; that is, a flexible elastic object that stores mechanical energy when it is twisted. When it is twisted, it exerts a force (torque) in the opposite direction, proportional to the amount (angle) it is twisted.

Other types of springs that may be used in various implementations of the IOL injectors of the present disclosure include, but are not limited to constant springs, variable springs, variable stiffness springs, flat springs, machined springs, serpentine springs, cantilever springs, hollow tubing springs, volute springs, hairsprings, leaf springs, V-springs, Belleville springs, constant-force springs, mainsprings, negator springs, progressive rate coil springs, rubber bands, spring washers, and wave springs, among others identifiable by persons of ordinary skill in the art.

Figure 5:
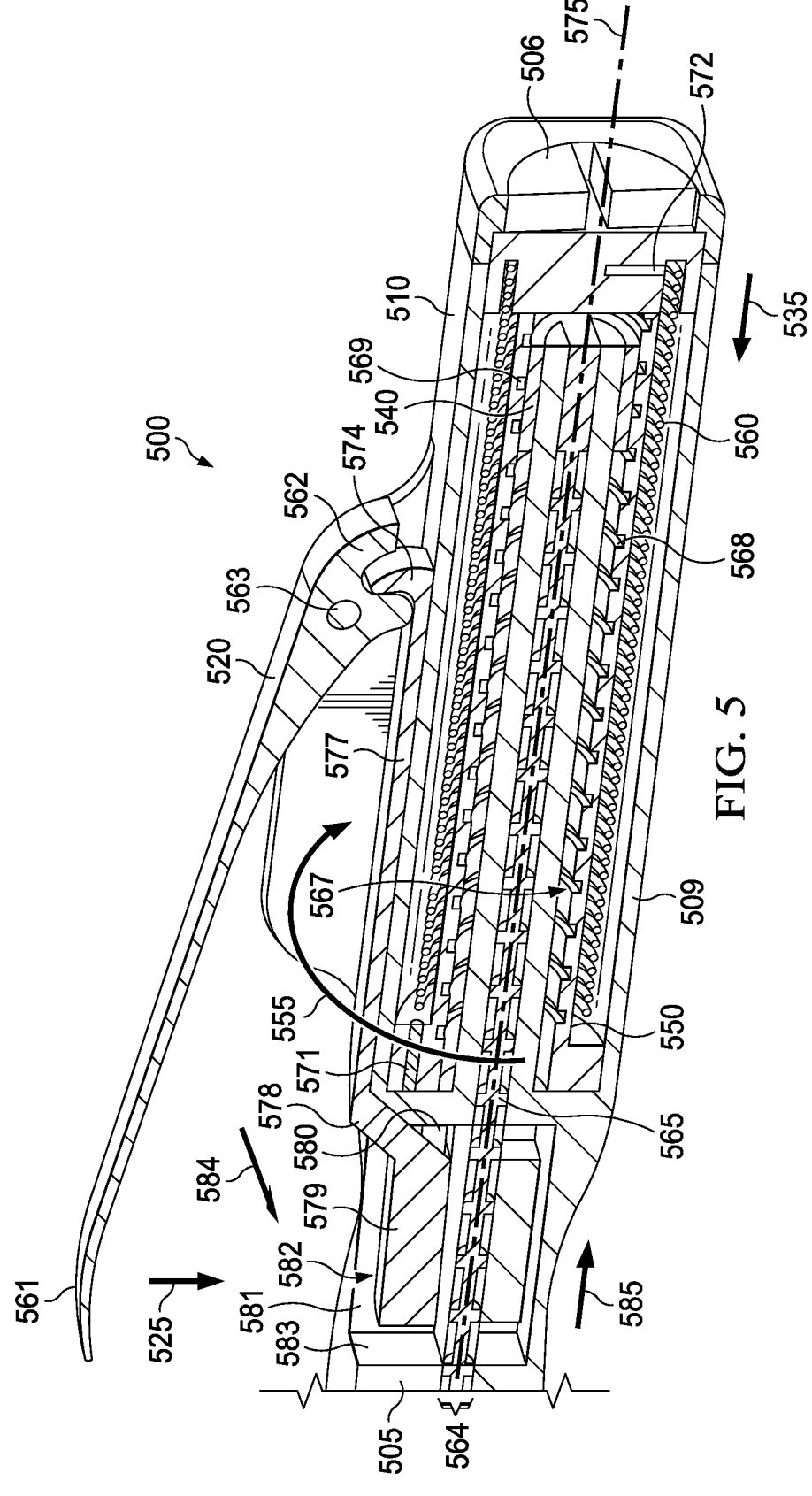
FIG. 5 is a cross-sectional view of an IOL injector actuated by an automatic driver.
Figure 6:
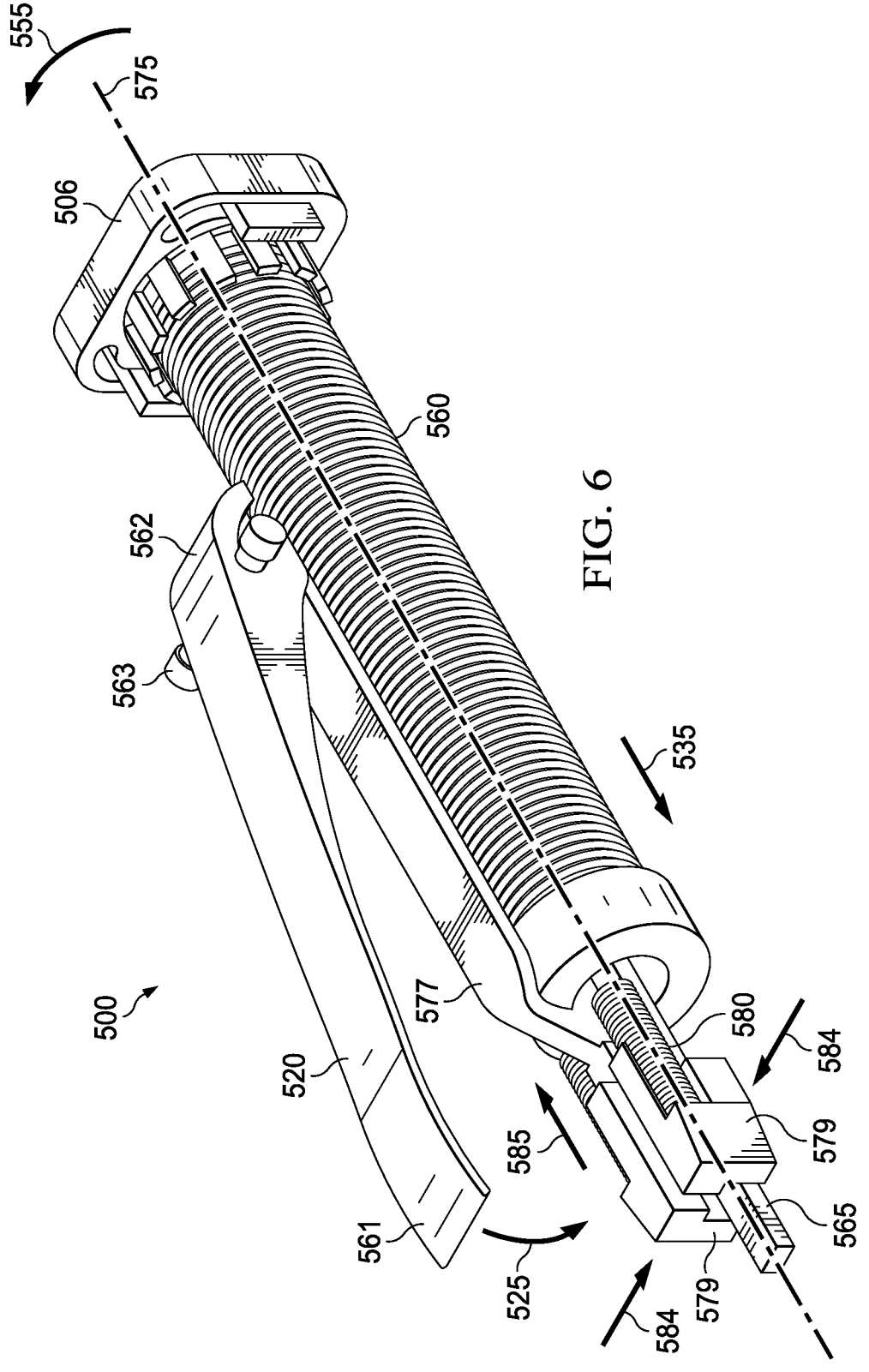
FIG. 6 is a perspective view of the IOL injector actuated by an automatic driver as shown in FIG. 5 with the cover removed.
Figure 7:
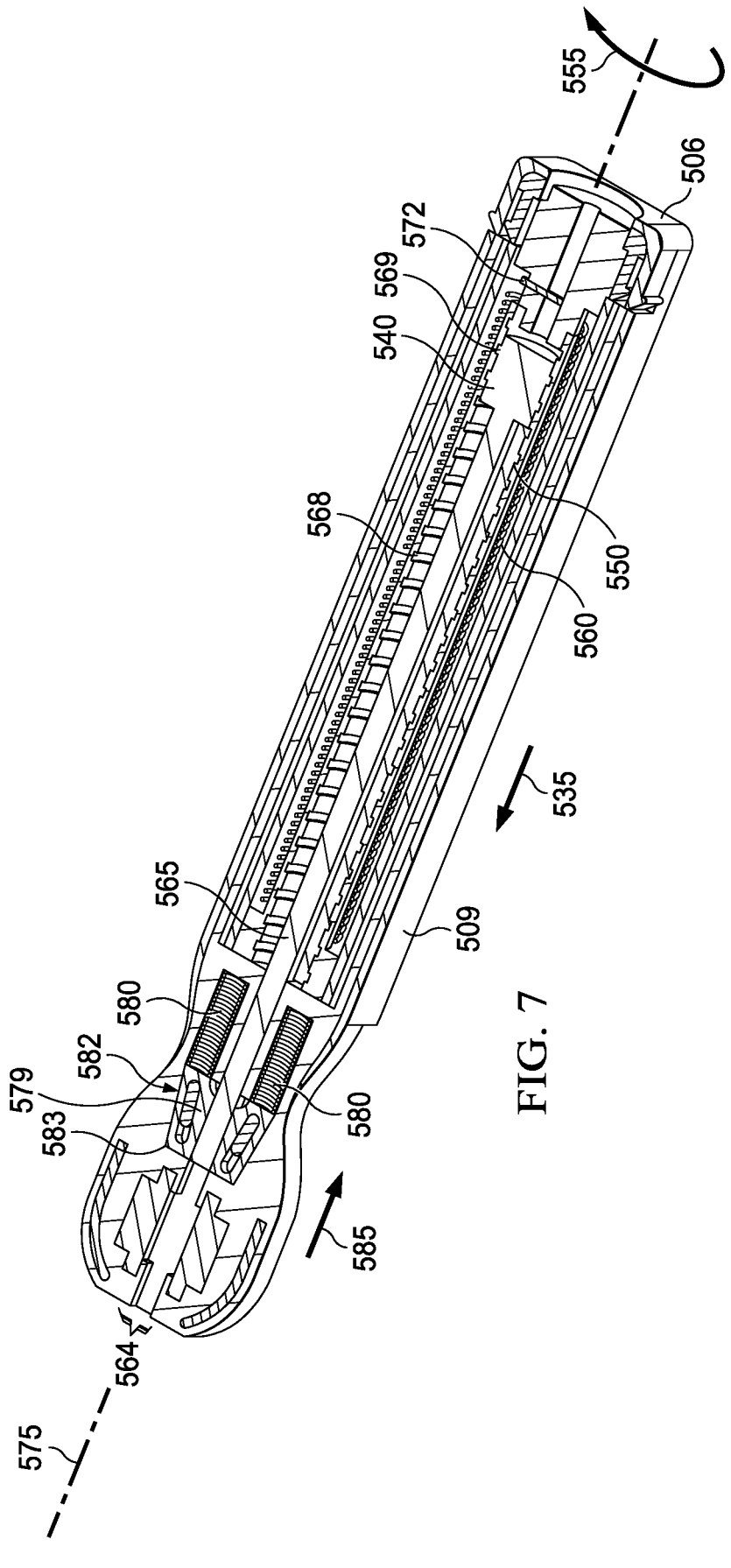
FIG. 7 is another cross-sectional view of the IOL injector actuated by an automatic driver as shown in FIG. 5 with the cover removed.

FIGS. 5, 6 and 7 show an example IOL injector 500 actuated by an automatic plunger advancement driver. In various implementations, the IOL injector 500 includes a injector body 509, including a main injector body 510 having a distal end 505 and a proximal end 506 and a nozzle (not shown) coupled to the distal end 505 of the main injector body 510. The injector body 510 defines a bore 564 extending from a proximal end 506 of the injector body 509 to a distal end (not shown) of the injector body 509.

The IOL injector 500 has a plunger 565 adapted to reciprocate through the bore 564 formed in the injector body. The plunger 565 is received within the bore 564 and moveable therein such that the plunger 565 is slideable within the bore 564. Particularly, the plunger 565 is slideable within bore 564 in order to advance an IOL, such as IOL 10, within the injector body 509.

The IOL injector 500 also includes a longitudinal axis 575. The longitudinal axis 575 may extend along the plunger 565 and define a longitudinal axis of the plunger 565.

As the plunger 565 is displaced distally within bore 564 in the direction of an arrow 535, the plunger 565 engages and advances an IOL, such as IOL 10, through the IOL injector 500 and out of the nozzle (not shown) into the eye.

The IOL injector 500 has a proximal portion of the plunger 565 concentrically disposed within a cylinder 550. An internal wall 567 of the cylinder 550 has a cylinder thread 568. A portion of the plunger 565 has a threaded cylinder-engaging portion 540 having a plunger thread 569. The cylinder thread 568 is adapted to engage with the plunger thread 569 and allows axial movement of the plunger 665 in the direction of arrow 535 in response to rotation of the cylinder 550 in the direction of arrow 555. The plunger 565 is rotationally fixed within the bore 564, such that the plunger 565 does not rotate in the direction of the arrow 555, but moves axially in the direction of arrow 535 in response to rotation of the cylinder 550 in the direction of arrow 555.

The cylinder 550 is concentrically disposed with a torsion spring 560. The torsion spring 560 contains stored potential rotational energy because the coiled windings of the torsion spring 560 are adapted to unwind in absence of a braking force applied to the driving mechanism that includes the torsion spring 560. At least one end of the torsion spring 560 is coupled to the cylinder 550. For example, the torsion spring may be coupled to the cylinder 550 at a distal end 571 and/or a proximal end 572 such that a release of the stored energy of the torsion spring 560 by unwinding, upon release of a braking force as described below, causes the cylinder 550 to rotate, for example in direction 555. In some implementations, one end of the torsion spring may be coupled to the injector body 509.

The IOL injector 500 has a braking mechanism adapted to prevent axial movement of the plunger 565. In some implementations, for example as shown in FIG. 5, the IOL injector 500 has a handle 520 rotatably coupled to the main injector body 510 at a pivot point 563 such that the handle 520 is adapted to rotate around the pivot point 563 in response to application of a force applied in the direction of an arrow 525. The handle has a distal end 561 and a proximal end 562. the proximal end 562 of the handle 520 is coupled to a proximal end 574 of a brake release arm 577 of the braking mechanism. A distal end 578 of the brake release arm 577 is coupled to one or more brake pads 579 adapted to contact the plunger 565 such that contact of the brake pads with the plunger provides a friction braking force in opposition of movement of the plunger 565. The brake pads 579 are axially movably disposed within a brake pad pocket 581 having a space formed between the plunger 565 and an inner wall 582. The inner wall 582 of the brake pad pocket 581 is tapered and is narrower a distal end 583 of the brake pad pocket 582 such that when the brake pads 579 are disposed at the distal end 583 of the brake pad pocket 582, the brake pad 579 is held tightly between the inner wall 582 and the plunger 565, providing transverse frictional braking force in the direction of arrow 584 toward the plunger 565, thereby preventing axial movement of the plunger 565.

In absence of application of force to the distal end 561 of the handle 520 in the direction of the arrow 525, the brake pads 565 are held at the distal end 583 of the brake pad pocket 581 in response to axial force applied by one or more compression springs 580 coupled between a proximal end of the brake pad 579 and the main injector body 510. Accordingly, decompression of the compression springs causes movement of the brake pads 579 in the direction of arrow 535 toward the distal end 583 of the braking pocket 581. In response to application of force in the direction of arrow 525 to the distal end 561 of the handle 520, the brake release arm 577 moves in the direction of arrow 585, compressing the compression spring 580 and pulling the brake pads 579 toward a proximal end of the braking pocket 581. The inner wall 582 at the proximal end of the braking pocket 581 tapers away from the plunger 565, such that when the brake pads 575 move toward the proximal end of the braking pocket 581, the brake pads 579 are not held tightly against the plunger 565, and the transverse frictional braking force is removed from the plunger 565.

Accordingly, is response to application of a force in direction 525 to the distal end 561 of the handle 520, the compression springs 580 are compressed and the braking mechanism is released from the plunger 565, allowing axial movement of the plunger 565 in the direction of the arrow 535 in response to release of the stored energy of the torsion spring 560 and rotation of the cylinder 550 in direction 555.

The torsion spring 560 is used as the energy source to axially advance plunger 565, which allows for single-handed use by a user. For example, the IOL injector 500 is adapted such that the user may hold the IOL injector 500 in a pencil grip and depress the distal end of the handle with an index finger. The automatic driving mechanism makes the IOL delivery process more consistent and predictable, while the braking mechanism mitigates against a risk of sudden IOL ejection.

The IOL injector 500 of FIGS. 5, 6, 7 and 8 can further include an IOL disposed within the hollow portion of the nozzle. When the plunger advances towards the nozzle, the plunger pushes and ejects the IOL out of the nozzle into the eye.

Figure 8:
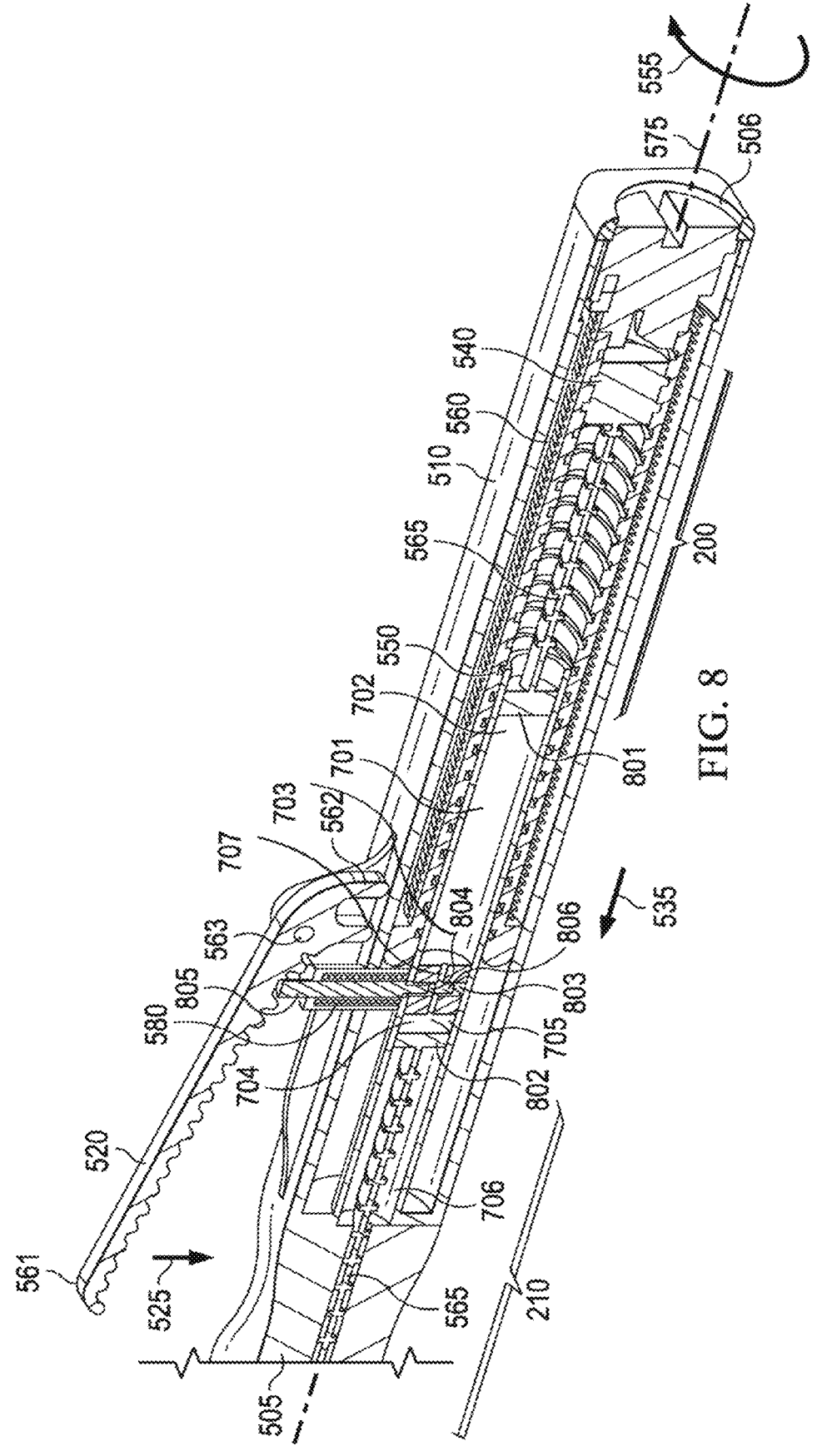
FIG. 8 is a perspective view of an exemplary IOL injector actuated by an automatic driver and having an exemplary hydraulic damping mechanism.

In some implementations, the IOL injector having the automatic driving mechanism can include a hydraulic damping mechanism, for example as shown in an exemplary implementation in FIG. 8. In some implementations, the exemplary hydraulic damping mechanism shown in FIG. 8 may function in a similar manner to the frictional braking mechanism described above and shown in FIGS. 5-7, but instead uses control of the flow rate of a hydraulic fluid to control the rate of advancement of the plunger 565. The hydraulic damping mechanism includes a proximal chamber 701 having a proximal end 702 and a distal end 703 and a distal chamber 704 having a proximal end 705 and a distal end 706. The plunger 565 includes a proximal portion 200 and a distal portion 210. The proximal portion 200 includes a proximal piston 801 slidably disposed within the proximal chamber 701 and movable from the proximal end 702 of the proximal chamber 701 to the distal end 703 of the proximal chamber 701 in response to movement of the threaded cylinder-engaging portion 540 of the plunger 565 in the direction of arrow 535. The distal end 703 of the proximal chamber 701 is coupled to an orifice 707 fluidically coupling the distal end 703 of the proximal chamber 701 to the proximal end 705 of the distal chamber 704 and allowing movement of a hydraulic fluid from the proximal chamber 701 to the distal chamber 704 in response to movement of the proximal piston 801. The proximal end of the distal portion 210 of the plunger 565 includes a distal piston 802 slidably disposed within the distal chamber 704 and movable from the proximal end 705 of the distal chamber 704 to the distal end 706 of the distal chamber 704 in response to movement of the fluid.

The fluid may be a mineral oil or other fluid suitable for hydraulic movement as described herein.

In some implementations, an internal diameter of the orifice 707 may be from 0.1 to 2 mm.

In some implementations, the orifice may include a one-way valve, such that axial movement of the fluid is in the direction of arrow 535, but not in a reverse axial direction.

In the exemplary implementation shown in FIG. 8, the handle 520 is coupled between the pivot point 563 and the distal end 561 to a first end 805 of a hydraulic flow barrier 803. A second end 806 of the hydraulic flow barrier 803 is slidably disposed within the orifice 707 such that in absence of a force applied to the handle 520 in the direction of arrow 525, the hydraulic flow barrier 803 prevents movement of the fluid through the orifice from the proximal chamber 701 to the distal chamber 704. The hydraulic flow barrier 803 includes a hydraulic flow gate 804 forming a passage adapted to allow movement of the fluid through the orifice 707 when the hydraulic flow gate 804 is disposed in the orifice. In absence of a force applied to the handle 520 in the direction of arrow 525, compression springs 580 disposed between the handle 520 and the orifice 707 apply a force in opposition to the direction of the arrow 525 and move the hydraulic flow gate 804 out of the orifice 707. In response to application of a force to the handle 520 in the direction of arrow 525, the hydraulic flow gate 804 is moved into the orifice and allows movement of the fluid through the orifice from the proximal chamber 701 to the distal chamber 704. Accordingly, in order to actuate axial movement of the plunger 565, a user may depress the handle 530 by applying a force in the direction of arrow 525, thereby positioning the hydraulic flow gate 804 within the orifice 707, allowing movement of the fluid from the proximal chamber 701 to the distal chamber 704 in the direction of the arrow 535 in response to movement of the torsion spring 560 rotating the cylinder in the direction 555 and axially moving the proximal portion of the plunger coupled to the cylinder threads via the plunger threads in the direction 535. The hydraulic damping mechanism thereby functions as a hydraulic brake. By depressing the handle 520 in the direction of the arrow 525, the user may release the hydraulic brake and allow advancement of the plunger 565 in the direction 535. Accordingly, the hydraulic damping mechanism allows a user to control the flow rate of the hydraulic fluid from the proximal chamber 701 to the distal chamber 704 and thereby control the transfer of rotational energy from the torsion spring 560 to axial movement of the plunger 565.

Accordingly, in some implementations, such as the exemplary IOL injectors described above and shown in FIGS. 5-8, a driving force to axially move the plunger through the bore of the IOL injector towards the distal end of the IOL injector body to deliver an IOL to an eye may be provided by the release of stored energy from a spring such as a torsion spring. In some implementations, therefore, axial movement of the plunger may be automatically driven by release of stored energy from a spring. Accordingly, in some implementations, plunger advancement may occur in absence of an axial force applied to the plunger by a user. In addition, in some implementations, a braking mechanism may be included in the IOL injector, wherein a user may release application of a braking force on the plunger to allow release of the stored energy from the spring to drive axial movement of the plunger.

In other implementations, such as the exemplary IOL injectors described below and shown for example in FIGS. 9-11C, a driving force to axially move the plunger through the bore of the IOL injector in a first axial direction toward the distal end of the IOL injector body to deliver an IOL to an eye may be provided by a first manual axial force applied to the plunger by a user and axial movement of the plunger may also be assisted by a second driving force provided by the release of stored energy from a spring. Accordingly, in various implementations, release of stored energy from the spring is adapted to assist axial movement of the plunger by transfer of the stored elastic energy from the spring into kinetic energy of axial movement of the plunger, herein referred to as a spring-assisted driving mechanism. For example, in some implementations, the release of the stored energy of the spring may be implemented by decompression of a compression spring. In other implementations, the release of stored energy of the spring may be implemented by contraction of a tension spring. In various implementations, springs that provide an assistive driving force to move the plunger toward the distal end of the IOL injector may be referred to as assistive springs. The spring-assisted driving mechanism may include one or more assistive springs. The assistive springs may be coupled at a first end of the spring directly or indirectly the plunger, and at a second end of the spring directly or indirectly to the injector body, such that release of the stored elastic energy from the assistive spring assists in driving axial movement of the plunger toward the distal end of the injector body. A non-limiting example described herein of an indirect coupling includes coupling of the spring to a gear, wherein the gear is rotatably coupled to the plunger having a rack adapted to mesh with the gear.

In addition, in some implementations, one or more springs may be included in an IOL injector in a spring damping mechanism adapted to provide a resistive force in an axial direction in opposition to axial movement of the plunger toward the distal end of the IOL injector body. For example, in some implementations, the resistive force may be implemented by compression of a compression spring. In other implementations, the resistive force may be implemented by stretching of a tension spring. Accordingly, in various implementations, the spring damping mechanism may be adapted to provide resistance to or damping of axial movement of the plunger by transferring the kinetic energy of plunger movement into stored elastic energy in the spring. In various implementations, springs that provide a resistive force in a second axial direction opposite to movement of the plunger toward the distal end of the IOL injector may be referred to as resistive springs or damping springs. The spring damping mechanism may include one or more resistive springs or damping springs. The damping springs may be coupled at a first end of the spring directly or indirectly the plunger, and at a second end of the spring directly or indirectly to the injector body, such that axial movement of the plunger toward the distal end of the injector body stores elastic energy in the damping spring. A non-limiting example described herein of an indirect coupling includes coupling of the spring to a gear, wherein the gear is rotatably coupled to the plunger having a rack adapted to mesh with the gear.

Accordingly, in various implementations, one or more assistive and/or resistive springs may be included in an IOL injector to provide a combination of assistive and/or resistive force to respectively assist in driving and/or dampening axial advancement of the plunger toward the distal end of the IOL injector body. In some implementations, the spring assisted driving force may include one or more spring driven gears. The term "spring driven gear" refers to a gear that is adapted to rotate in response to release of stored energy from a spring. Thus, in various implementations, a spring driven gear included in an IOL injector may be an assistive spring driven gear or a damping spring-driven gear. The term "assistive spring-driven gear" refers to a gear that assists in driving axial movement of the plunger toward the distal end of the injector body through release of stored energy from a spring, converting the released energy into rotational movement of the gear, wherein the gear is coupled to the plunger typically through meshing of teeth of the gear with teeth of a rack disposed on the plunger, and adapted to assist in driving axial movement of the plunger. In contrast, the term "damping spring-driven gear" refers to a gear that provides a force in opposition to axial movement of the plunger toward the distal end of the injector body by converting the kinetic energy of axial plunger movement into stored energy in the spring typically. through meshing of teeth of the gear with teeth of the rack disposed on the plunger.

Figure 9A:
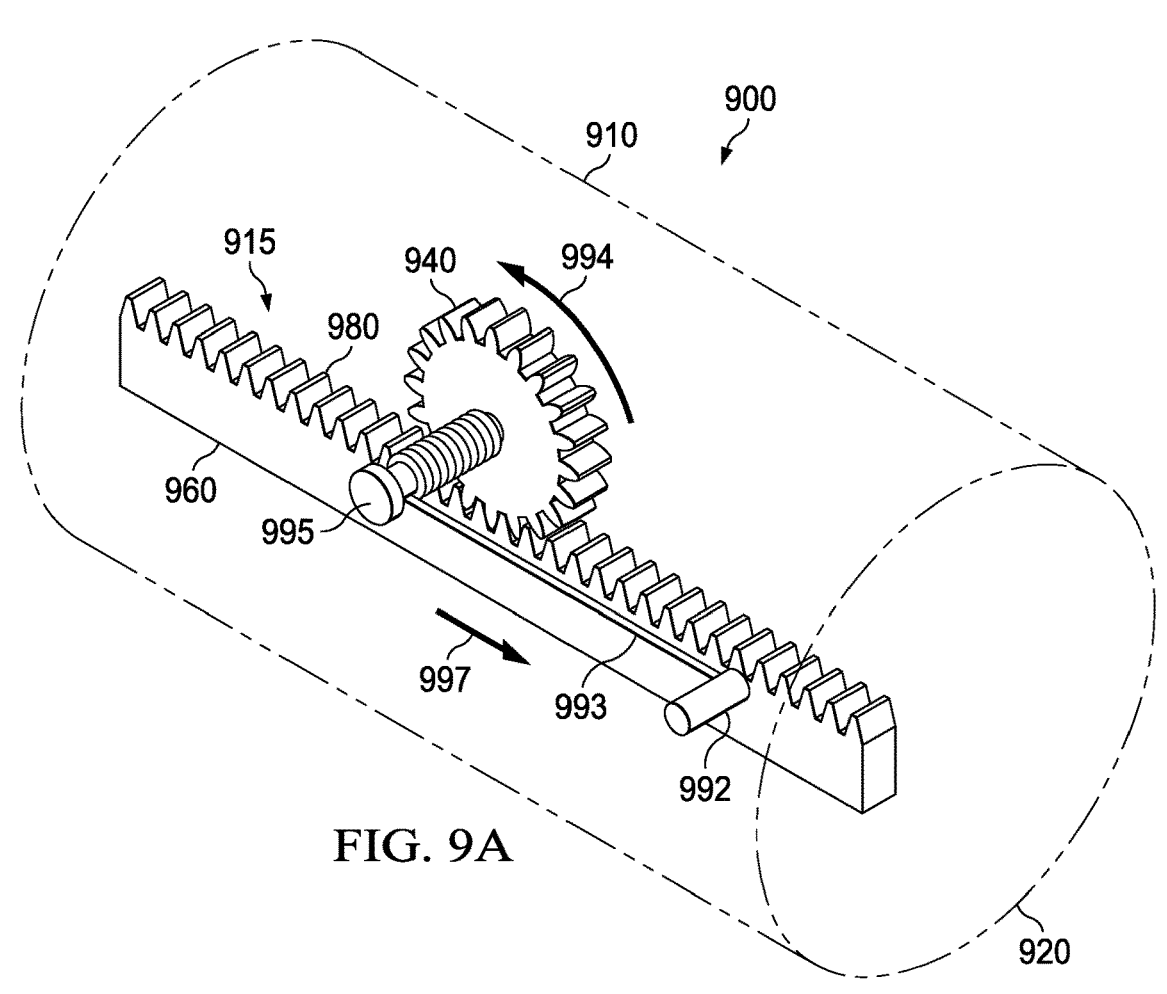
FIG. 9A is a schematic of an example IOL injector with rotational spring gear assisted manual drive force.

For example, FIG. 9A is a schematic showing a view of an exemplary implementation of a spring-driven gear that may be used in various implementations in the IOL injector. FIG. 9A shows an IOL injector 900 having an injector body 910 defining a bore 915 and a plunger 960 adapted to reciprocate through the bore 915 and moveable therein such that the plunger 960 is slideable within the bore 915. The plunger 960 includes a rack 980 disposed thereon including a plurality of teeth that are configured to mesh with teeth of the first gear 940 so that the plunger 960 is axially movable in response to rotation of the first gear 940. The first gear 940 is fixedly coupled to a shaft 995 that is rotatably coupled to the injector body 910. The first gear 940 is configured to rotate in the direction of an arrow 994 in response to contraction of a spring having stored elastic energy. For example, an exemplary spring shown in FIG. 9A is an elastic band such as a rubber band 993 wound up around the shaft 995 at a first end and coupled to the injector body 910 at a second end 992. For example, as shown in FIG. 9A, release of the stored elastic energy in the rubber band 993, by unwinding of the rubber band 993 around the shaft 995, causes the first gear 940 to rotate in the direction of arrow 994, and the plunger to move in response in the direction of the arrow 997 toward distal end 920 of the injector body. In contrast, movement of the plunger 960 in an axial direction opposite to the arrow 997 would cause the first gear 940 to rotate in the opposite direction to the arrow 994, thereby winding up the rubber band 993 around the shaft 995 and thereby causing the kinetic energy of the plunger 960 movement to be stored as elastic energy in the rubber band 993, wherein the rubber band would be providing a resistive force against axial movement of the plunger 960. In some implementations, a spring-driven gear may be configured to sequentially function both as an assistive spring-driven gear and as a damping spring-driven gear.

Figure 9B:
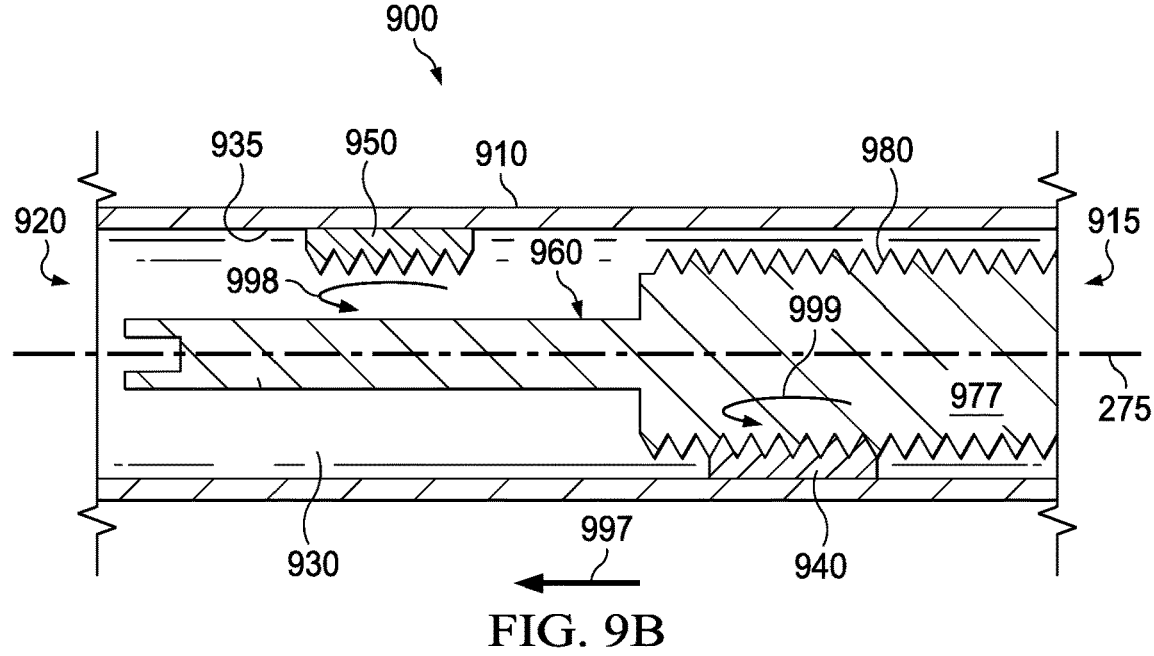
FIG. 9B is a cross-sectional view of another example IOL injector with rotational spring gear assisted manual drive force.

FIG. 9B shows a cross-sectional view of an exemplary IOL injector 900 having an assistive spring driven gear and a damping spring driven gear. The IOL injector 900 includes an injector body 910 having a bore 930 defined by an interior wall 935 of the injector body 910. The exemplary IOL injector 900 may have one or more assistive spring-driven gears adapted to transfer release of stored energy from a spring into axial movement of the plunger. For example, within the bore 930, a first gear 940 is disposed on the interior wall 935 of the injector body 910 at a proximal end 915 of the injector body 910. The first gear 940 may be an assistive spring-driven gear. Accordingly, for example, the first gear 940 may be coupled to a spring having stored elastic energy, wherein the first gear 940 is adapted to rotate in response to release of the stored elastic energy from the coupled spring. The IOL injector 900 has a plunger 960 movable within the bore 930 of the injector body 910 in a first direction indicated by arrow 997 toward the distal end 920 of the injector body 910 in response to an axial force applied to the proximal end 977 of the plunger 960. The plunger 960 includes a rack 980 disposed thereon including a plurality of teeth that are configured to mesh with teeth of the first gear 940, wherein the plunger 960 is axially movable in response to rotation of the first gear 940.

Application of force by a user to the proximal end 977 of the plunger 960 to advance the plunger 960 through the bore 930 towards a distal end 920 of the injector body 910 may be assisted by release of the stored elastic energy from the spring coupled to the first gear 940, thereby assisting advancement of the plunger 960 through the bore 930.

In some implementations, the IOL injector may include a second spring-driven gear 950.

In FIG. 9B, the first gear 940 and the second gear 950 are shown such that the axis of rotation of the first gear 940 and the second gear 950 are indicated by arrows 998 and 999, respectively.

In some implementations, the second spring-driven gear 950 may be configured as a resistive spring-driven gear. Accordingly, in some implementations, the second gear 950 may be coupled to a spring having little or no stored elastic energy prior to engagement of the second gear 950 with the rack 980 of the plunger 960. Upon continued application of axial force by the user to the plunger 960 in the direction of the arrow 997, the rack 980 is configured to mesh with the teeth of the second gear 950 and cause the second gear to rotate. In response to rotation of the second gear 950, elastic energy is stored in the spring coupled to the second gear 950. The transfer of the kinetic energy of the plunger 960 movement into stored elastic energy by the second gear 950 provides a resistive force to axial movement of the plunger 960.

In some implementations, the first and second gears 940, 950 can be rotational spring driven gears. In some implementations, one or more of the gears can be replaced by helical springs, for example as described in the exemplary implementations shown in FIG. 10 below.

In some implementations, the second gear 950 can be replaced by a syringe-type damper adapted to provide frictional resistance against axial movement of the plunger 960.

Accordingly, in some implementations, an IOL injector may include one or more spring-driven gears that provide an assistive axial force and/or a resistive axial force in relation to axial plunger movement. For example, in some implementations, as shown in FIG. 9B, the first gear 940 may be configured to provide a reduction in force required to be applied by a user to advance an IOL through the injector 900. In some implementations, the second gear 950 may be configured to mitigate against a sudden drop in the force experienced by the user upon ejection of the IOL from the injector 900. Therefore, in various implementations, one or more spring-driven gears included in an IOL injector may provide a consistent and smooth axial driving force to assist a user in advancing an IOL through the IOL injector, while the damping function decreases the risk of sudden ejection of the IOL, and provides higher reliability for the user.

Accordingly, in some implementations, upon application of an axial force by a user to the plunger to advance the plunger toward the distal end of the injector body, the rack engages the first gear and the first gear applies a force to assist further advancement of the plunger through the bore. In addition, in some implementations, upon application of further axial force by a user to the plunger to advance the plunger toward the distal end of the injector body, the rack engages the second gear and the second gear applies a force to resist further advancement of the plunger through the bore.

In some implementations, the first gear 940 and the second gear 950 may be respectively coupled to springs having different elastic or other mechanical properties. For example, in some implementations, the spring coupled to the first gear 940 may have a greater force of elastic energy release than the spring coupled to the second gear 950. For example, the spring coupled to the first gear 940 may have, or have about, 1.5 times the force of the spring coupled to the second gear 950. In some implementations, the spring coupled to the first gear 940 may have, or have about, 1, 2, 3, or 4 times the force of the spring coupled to the second gear 950.

FIG. 10 is a schematic showing a cross-sectional view of another exemplary IOL injector 1000 having a helical spring assisted axial drive force. The exemplary IOL injector 1000 includes an injector body 1010 with a bore 1030 defined by an interior wall 1035, and a distal end 1020 and a proximal end 1025. At least one stop 1040 is disposed on the distal end 1020 of the interior wall 1035, each stop 1040 having a pin 1045 that projects into the bore 1030.

A first helical spring 1050 is disposed within the interior wall 1035 of the IOL injector 1000, and a second helical spring 1060 disposed within the first helical spring 1050.

The IOL injector 1000 includes a plunger 1070 movable within the bore 1030 in response to an axial force applied to the plunger 1070 such that the plunger 1070 is slideable within the bore 1030, the plunger 1070 having a distal end 1075 and a proximal end 1077. A user can apply axial force to the proximal end 1077 of the plunger 1070 to advance the plunger through the injector body 1010, as shown by direction 1090.

In an exemplary implementation shown in FIG. 10, the plunger 1070 is disposed within the second spring 1060, and the second spring is disposed within a sheath 1001. For example, the sheath 1001 may be a cylinder sized to be disposed within the inner wall 1035 of the injector body 1010 and surrounding a portion of the plunger 1070. A portion of the bore 1030 is defined within the sheath 1001 allowing the plunger 1070 to move slideably within the sheath 1001. A proximal end 1002 of the second spring 1060 is coupled to the plunger 1070. A distal end 1003 of the second spring 1060 is coupled to the sheath 1001. In some implementations, the second helical spring 1060 may be an assistive spring. For example, the second helical spring 1060 may be a tension spring having stored elastic energy that is released upon contraction of the tension spring. For example, as shown in FIG. 10, when the second spring 1060 is a tension spring, the plunger 1070 is adapted to move in direction 1090 in response to contraction of the second spring 1060.

The sheath is slideably movable in the bore 1030 between the stops 1040 in response to axial force applied to the plunger 1070 in direction 1090. In particular, in some implementations, the sheath is slideably movable in the bore 1030 between the stops 1040 in upon full compression of the second spring 1060 and in response to further axial force applied to the plunger 1070 in direction 1090. Accordingly, the second spring 1060 is coupled at the proximal end of the second spring to the plunger 1070 and coupled indirectly at the distal end of the second spring 1060 to the injector body 1010.

In some implementations, the first spring 1050 may be a resistive spring. For example, in FIG. 10, the sheath 1001 is disposed within the first spring 1050. A proximal end 1004 of the first spring 1050 is coupled to the sheath 1001. A distal end 1005 of the first spring 1050 is coupled to the stops 1040. Accordingly, the first spring 1050 is coupled indirectly at the proximal end of the first spring 1050 to the plunger 1070 and coupled indirectly at the distal end of the first spring 1050 to the injector body 1010. In some implementations, for example, the first helical spring 1060 may be a compression spring adapted to store elastic energy upon compression of the compression spring. For example, as shown in FIG. 10, when the first spring 1060 is a compression spring, the first spring is adapted to compress in response to axial movement of the plunger 1070 in direction 1090. Accordingly, compression of the first spring provides a damping resistive force in the direction of arrow 1055 against axial movement of the plunger in direction 1090. In particular, in some implementations, as shown in FIG. 10, while the sheath 1001 slideably moves through the bore 1030 between the stops 1040, the first spring 1050 may compress, providing a resistive damping force against axial movement of the sheath 1001 and the plunger 1070.

Accordingly, the second helical spring 1060 provides a reduction in the peak force necessary for the user to advance the IOL through the injector 1000. The first helical spring 1050 may be configured to provide a damping force to reduce the probability of a sudden drop in the force experienced by the user upon ejection of the IOL from the injector 1000.

Figure 11A:
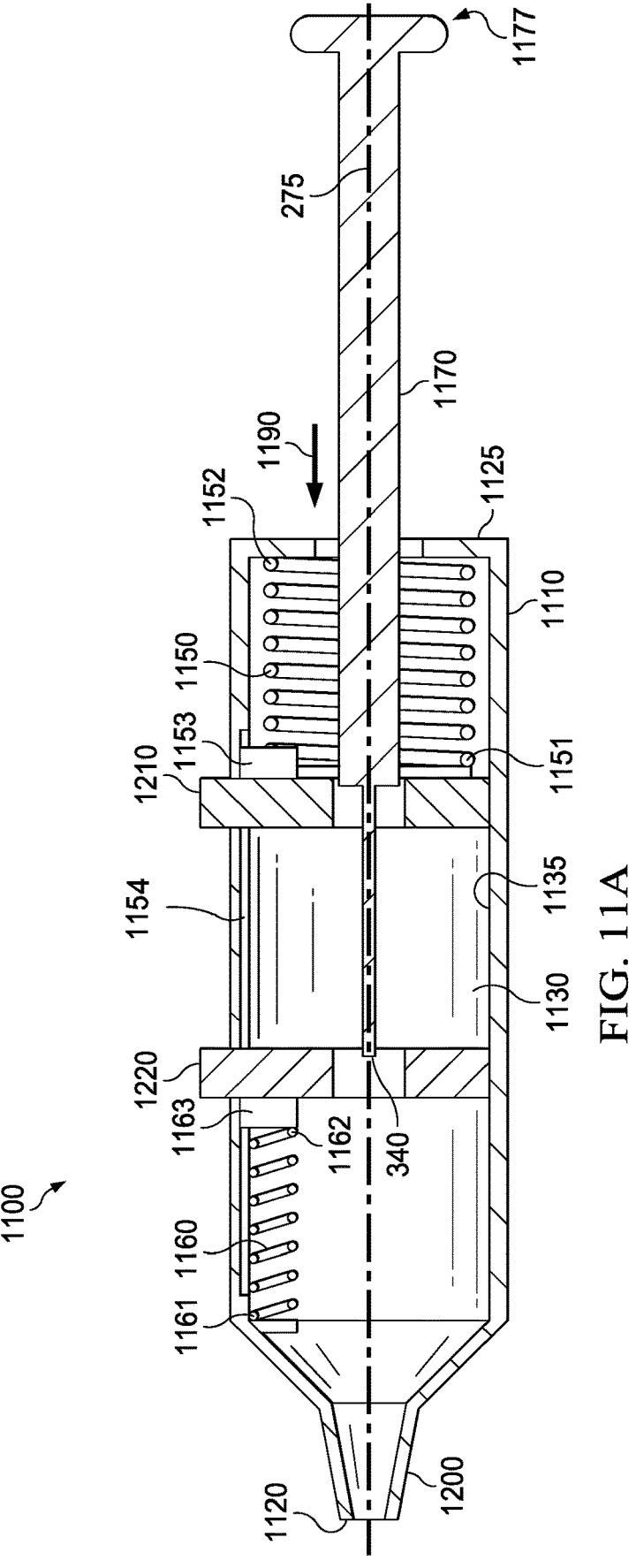
FIG. 11A is a cross-sectional view of still another example IOL injector with compressive spring and stops to assist a manual drive force.
Figure 11B:
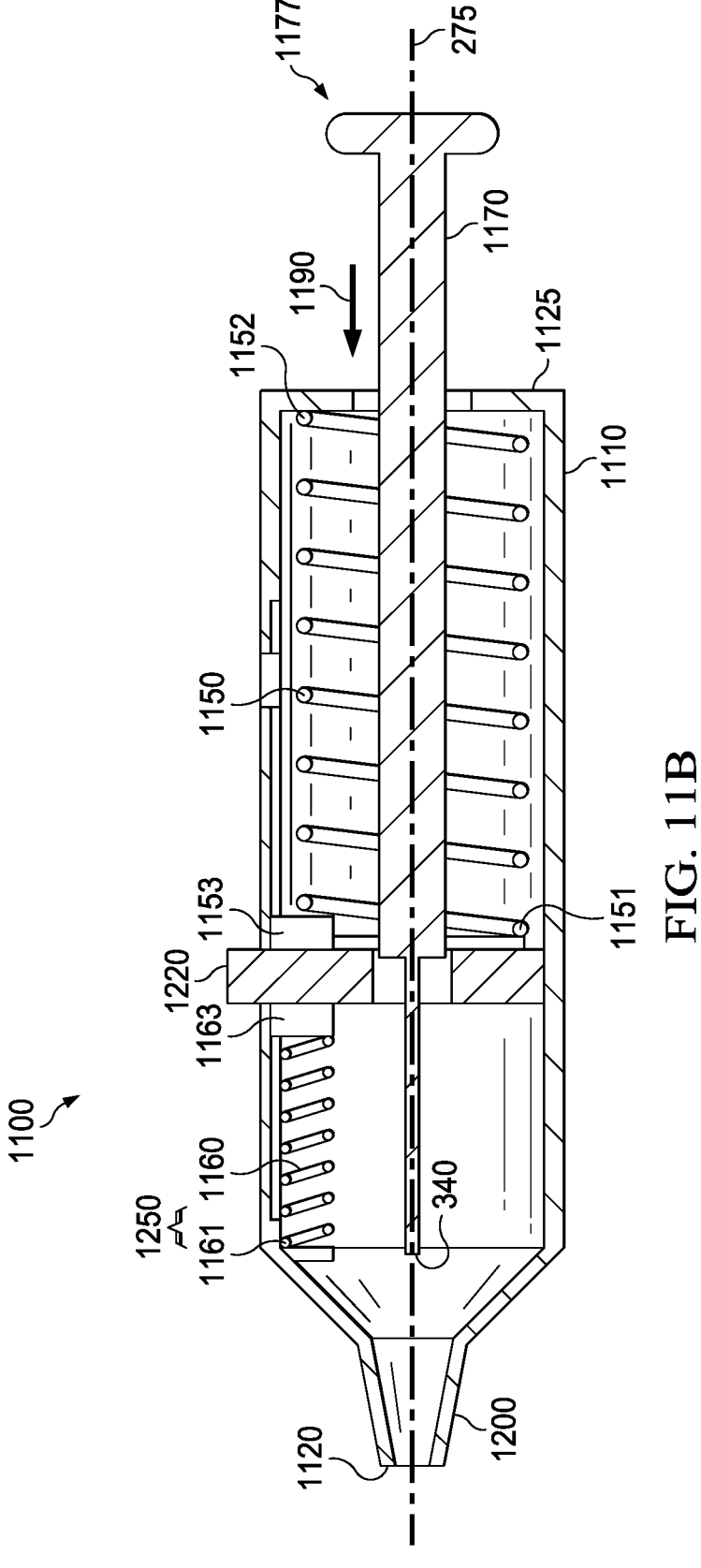
FIG. 11B is another cross-sectional view of the example IOL injector of FIG. 11A with compressive spring and stops to assist a manual drive force.
Figure 11C:
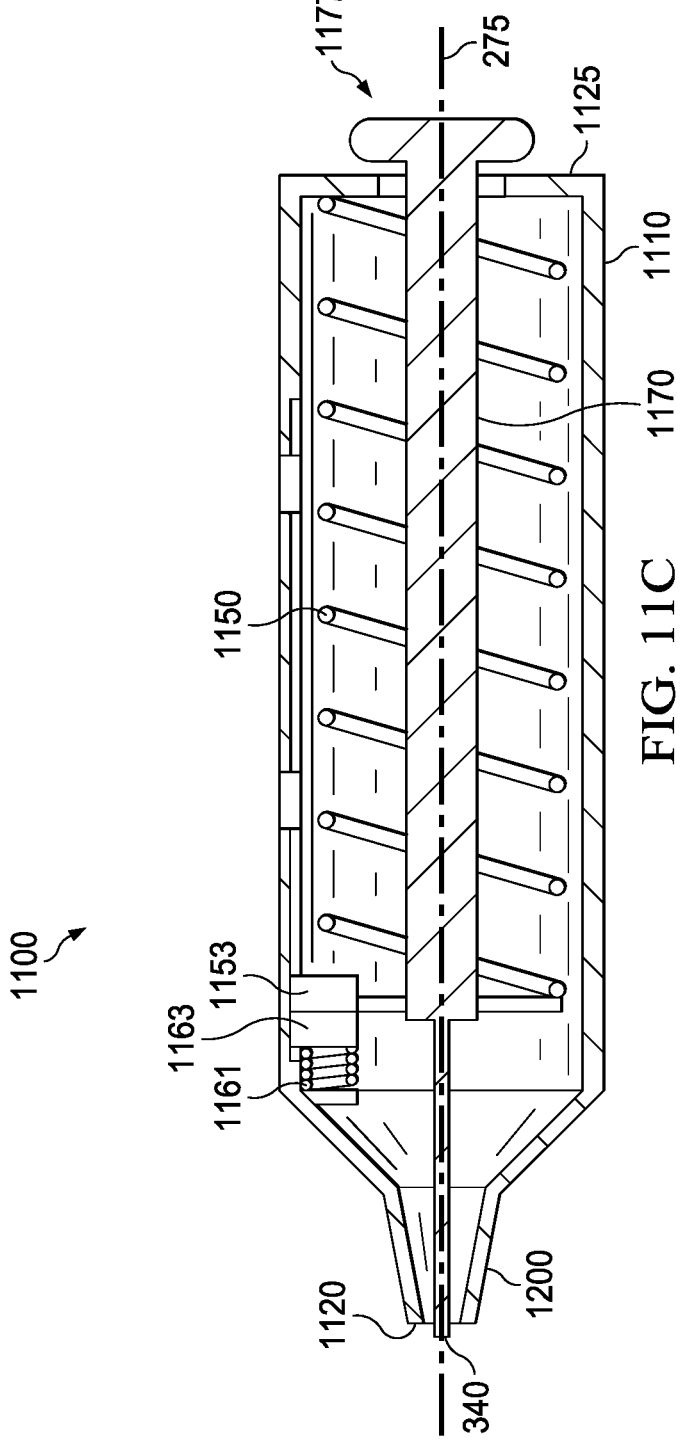
FIG. 11C is yet another cross-sectional view of the example IOL injector of FIG. 11A with compressive spring and stops to assist a manual drive force.

FIG. 11A to FIG. 11C are schematics of another example of an IOL injector that includes an assistive spring and a damping spring. The exemplary IOL injector 1100 includes an injector body 1110 having a bore 1130 defined by an interior wall 1135 of the injector body 1110. The injector body 1110 has a distal end 1120 and a proximal end 1125. A nozzle 1200 is disposed at the distal end 1120 of the injector body 1110.

The IOL injector 1100 further includes a plunger 1170, having a distal end with a plunger tip 340 and a proximal end 1177. The plunger 1170 is received within the bore 1130 and is moveable therein such that the plunger 1170 is slideable within the bore 1130 in response to an axial force applied to the distal end 1177, as shown by direction 1190.

A first helical spring 1150 is disposed within the bore 1130 near the proximal end 1125. In some implementations, the first helical spring 1150 is an assistive spring. For example, the first helical spring 1150 may be a compression spring. In some implementations, in an initial configuration, the first helical spring is a compression spring that is compressed to, or to about, 40-50% of its resting length in a resting position. For example, as shown in FIG. 11A, a distal end 1151 of the first helical spring 1150 is coupled to the plunger 1170. A proximal end 1152 of the first helical spring 1150 is coupled to the proximal end 1125 of the injector body 1110. In some implementations, the proximal end 1152 of the first helical spring 1150 may be coupled to a proximal portion of the injector body 1110, for example at a location adjacent to the proximal end 1125 of the injector body 1110. In some implementations, the distal end 1151 of the first helical spring 1150 is also coupled to a first contact tab 1153 adapted to contact a first removable stop 1210 disposed within the bore 1130 when the IOL injector is in a first configuration. In other implementations, the first contact tab 1153 may be absent and the distal end 1151 of the first helical spring 1150 may be adapted to contact the first removable stop 1210 directly. In the first configuration, for example as shown in FIG. 11A, the first contact tab 1153 is in contact with the first stop 1210, which maintains the first helical spring 1150 in a relatively compressed state having stored elastic energy. As shown in FIG. 11B, in a second configuration, in response to removal of the first stop 1210, the first helical spring 1150 is configured to expand, typically to, or to about, 75% of the resting length of the first helical spring in its resting position, thereby assisting movement of the plunger in the direction of arrow 1190. The first helical spring 1150 is adapted to expand until the first contact tab 1153 contacts a second removable stop 1220 disposed within the bore 1130. In some implementations, the plunger tip 340 may be proximally adjacent to an IOL dwell position 1250 when the first contact tab 1153 is in contact with the second removable stop 1220. In some implementations, the first contact tab 1153 may be adapted to slide axially within a channel 1154 disposed within the injector body 1110.

Accordingly, in some implementations, the first helical spring 1150 provides an assistive force to the axial motion of the plunger in the direction 1190 after the first stop is removed.

In some implementations, a second helical spring 1160 may be disposed within the bore 1130 near the distal end 1120 of the injector body 1110. A distal end 1161 of the second helical spring 1160 is coupled to the injector body 1110 adjacent to the distal end 1120 of the injector body 1110, for example at a location adjacent to the distal end of the main injector body. A proximal end 1162 of the second helical spring 1160 is coupled to a second contact tab 1163 adapted to contact the second removable stop 1220. In other implementations, the second contact tab 1163 may be absent and the proximal end 1162 of the first helical spring 1160 may be adapted to contact the second removable stop 1220 directly. In the second configuration, for example as shown in FIG. 11A, the second contact tab 1153 may be in contact with the second stop 1220, which in some implementations may maintains the second helical spring 1160 in a relatively uncompressed state, or resting position, having little or no stored elastic energy. In some implementations, the second contact tab 1163 may be adapted to slide axially within the channel 1154 disposed within the injector body 1110.

In a third configuration, the second removable stop 1220 may be removed to allow the plunger 1170 to be further advanced axially in the direction 1190 such that the plunger tip 340 moves from a location proximally adjacent to the IOL dwell position 1250 to the distal end 1120 of the injector body 1110, thereby ejecting an IOL 10 into an eye. In the third configuration, when the second removable stop 1220 is removed from the injector body 1110, the first contact tab 1153 and the second contact tab 1163 are adapted to contact each other as shown in FIG. 11C, or if the tabs are absent, the first helical spring and the second helical spring may contact each other. Accordingly, during axial movement of the plunger tip 340 from the location proximally adjacent to the IOL dwell position to the distal end 1120 of the injector body 1110, the first helical spring 1150 and the second helical spring 1160 act against each other, with the first helical spring 1150 extending its final approximately 25% to full extension. At the same time, the second helical spring 1160 is compressed from a relatively uncompressed state or resting position to a compressed state. In particular, when the plunger tip 340 is advancing the IOL out of the nozzle 1200, the second helical spring 1160 is adapted to be near its maximum compression to ensure the user is now pushing against it to express the IOL at the nozzle exit. The damping force provided by the second helical spring has the advantage of decreasing the probability of sudden ejection of the IOL.

Various implementations of the IOL injectors described herein and within the scope of the present disclosure may be configured to deliver an IOL base and/or an IOL optic of a multi-piece IOL, or a 1-piece IOL. Various implementations of the IOL injectors described herein may be used with an IOL base and/or the optic that are manually loaded into the IOL injector by a user or pre-loaded there prior to delivery by a user.

Non-limiting examples of IOL injectors that may be adapted according to the present disclosure include those described in U.S. Pat. No. 7,156,854 and U.S. Patent Application Publication No. 2016/0256316, the disclosures of each being incorporated herein by reference in their entireties.

Although the disclosure provides numerous examples, the scope of the present disclosure is not so limited. Rather a wide range of modification, change, and substitution is contemplated in the foregoing disclosure. It is understood that such variations may be made to the foregoing without departing from the scope of the present disclosure.

What is claimed is:

1. An intraocular lens (IOL) injector, comprising:
    an injector body having a proximal end and a distal end including:
        a main injector body having a distal end and a proximal end;
        a nozzle coupled to the distal end of the main injector body; and
        a bore extending from the proximal end of the injector body to the distal end of the injector body; and
    a plunger having a proximal portion and a distal portion, the plunger slideably disposed and rotationally fixed within the bore, the plunger adapted to advance an IOL along a longitudinal axis of the IOL injector; and
    an automatic plunger advancement driver having:
        a cylinder concentrically disposed around the proximal portion of the plunger, the cylinder having a thread adapted to rotatably engage with a plunger thread in the proximal portion of the plunger; and
        a torsion spring having stored rotational energy, the torsion spring concentrically disposed around the cylinder,
        wherein at least one end of the torsion spring is coupled to the cylinder such that in response to a release of the stored rotational energy, the cylinder is configured to rotate around the longitudinal axis and the plunger moves axially toward the distal end of the injector body.

2. The IOL injector of claim 1, further comprising:

a hydraulic damping mechanism including:

a proximal chamber having a proximal end and a distal end;

a distal chamber having a proximal end and a distal end;

an orifice fluidically coupling the proximal chamber to the distal chamber;

the proximal portion of the plunger having a proximal piston slideably disposed within the proximal chamber; and the distal portion of the plunger having a distal piston slideably disposed within the distal chamber;

wherein:

the proximal piston is movable from the proximal end of the proximal chamber to the distal end of the proximal chamber in response to movement of a threaded cylinder-engaging portion of the plunger;

the orifice allows movement of a hydraulic fluid from the proximal chamber to the distal chamber in response to movement of the proximal piston; and the distal piston is movable from the proximal end of the distal chamber to the distal end of the distal chamber in response to movement of the fluid.

3. The IOL injector of claim 2, further comprising:

a braking mechanism configured to prevent axial movement of the plunger, including:

a handle having a proximal end and a distal end and rotatably coupled to the injector body at a pivot point disposed between the proximal end and the distal end of the handle in response to a force applied to the handle;

a hydraulic flow barrier having a first end coupled to the handle and a second end slideably disposed within the orifice and adapted to prevent movement of the fluid through the orifice from the proximal chamber to the distal chamber in absence of a force applied to the handle;

a hydraulic flow gate forming a passage adapted to allow movement of the fluid through the orifice when the hydraulic flow gate is disposed in the orifice; and compression springs disposed between the handle and the orifice, the compression springs adapted to move the hydraulic flow gate out of the orifice;

wherein:

in response to application of a force to the handle, the hydraulic flow gate is moved into the orifice and allows movement of the fluid through the orifice from the proximal chamber to the distal chamber.

4. The IOL injector of claim 1 further comprising an IOL disposed within a hollow portion of the nozzle, such that axial movement of the plunger towards the distal end of the injector body causes the IOL to be ejected from the nozzle.

* * * * *